US012453873B2

(12) United States Patent
Adams

(10) Patent No.: US 12,453,873 B2
(45) Date of Patent: Oct. 28, 2025

(54) DEAD AIR MASK FOR KILLING MICROORGANISMS IN AIR BREATHED BY A WEARER OF THE MASK

(71) Applicant: Michael A. Adams, Cypress, TX (US)

(72) Inventor: Michael A. Adams, Cypress, TX (US)

( * ) Notice: Subject to any disclaimer, the term of this patent is extended or adjusted under 35 U.S.C. 154(b) by 649 days.

(21) Appl. No.: 17/913,135

(22) PCT Filed: Mar. 19, 2021

(86) PCT No.: PCT/US2021/023358
§ 371 (c)(1),
(2) Date: Sep. 20, 2022

(87) PCT Pub. No.: WO2021/189023
PCT Pub. Date: Sep. 23, 2021

(65) Prior Publication Data

US 2023/0132702 A1 May 4, 2023

Related U.S. Application Data

(60) Provisional application No. 63/155,608, filed on Mar. 2, 2021, provisional application No. 62/992,554, filed on Mar. 20, 2020.

(51) Int. Cl.

| | |
|---|---|
| ***A61L 9/20*** | (2006.01) |
| ***A62B 18/00*** | (2006.01) |
| ***A62B 18/02*** | (2006.01) |
| ***A62B 23/02*** | (2006.01) |

(52) U.S. Cl.
CPC ................ *A62B 23/02* (2013.01); *A61L 9/20* (2013.01); *A62B 18/006* (2013.01); *A62B 18/025* (2013.01)

(58) Field of Classification Search
CPC ....... A61L 9/20; A62B 18/006; A62B 18/025; A62B 18/02; A62B 18/04; A62B 18/045; A62B 23/02; A41D 13/11
See application file for complete search history.

(56) References Cited

U.S. PATENT DOCUMENTS

| | | | | |
|---|---|---|---|---|
| 5,165,395 | A * | 11/1992 | Ricci ......................... | A61L 9/20 55/DIG. 35 |
| 6,055,666 | A | 5/2000 | Eklund et al. | |
| 2007/0101867 | A1* | 5/2007 | Hunter .................. | A62B 23/02 96/224 |
| 2007/0102280 | A1 | 5/2007 | Hunter et al. | |

(Continued)

*Primary Examiner* — Joseph D. Boecker
*Assistant Examiner* — Brian T Khong
(74) *Attorney, Agent, or Firm* — McCutcheon Joseph, PLLC

(57) ABSTRACT

A wearable mask includes a light module attached to a cover. The light module includes an inlet for receiving air to be breathed in by the person, and an outlet that faces the person. Airflow paths extend between the inlet and the outlet, and receive air to be breathed in by the person. An ultraviolet (UV-C) light source emits anti-microbial light into the one or more airflow paths at a wavelength that kills microorganisms in the air in the one or more airflow paths. Walls at the inlet and outlet each includes one or more slits through which the air passes. The one or more slits of each wall are offset relative to the one or more slits of an adjacent wall to form staggered airflow paths that allow the air to pass through offset slits, but blocks the anti-microbial light from passing through the offset slits.

20 Claims, 6 Drawing Sheets

(56) References Cited

U.S. PATENT DOCUMENTS

| | | | | |
|---|---|---|---|---|
| 2010/0132715 | A1* | 6/2010 | Litz | A62B 7/10 128/207.12 |
| 2010/0307332 | A1* | 12/2010 | Yuen | B03C 3/383 96/25 |
| 2016/0001106 | A1 | 1/2016 | Zhou et al. | |
| 2016/0001108 | A1* | 1/2016 | Zhou | A62B 7/10 128/863 |
| 2018/0078798 | A1 | 3/2018 | Fabian et al. | |
| 2018/0264161 | A1* | 9/2018 | Welch | A41D 13/1192 |

* cited by examiner

Fig. 6
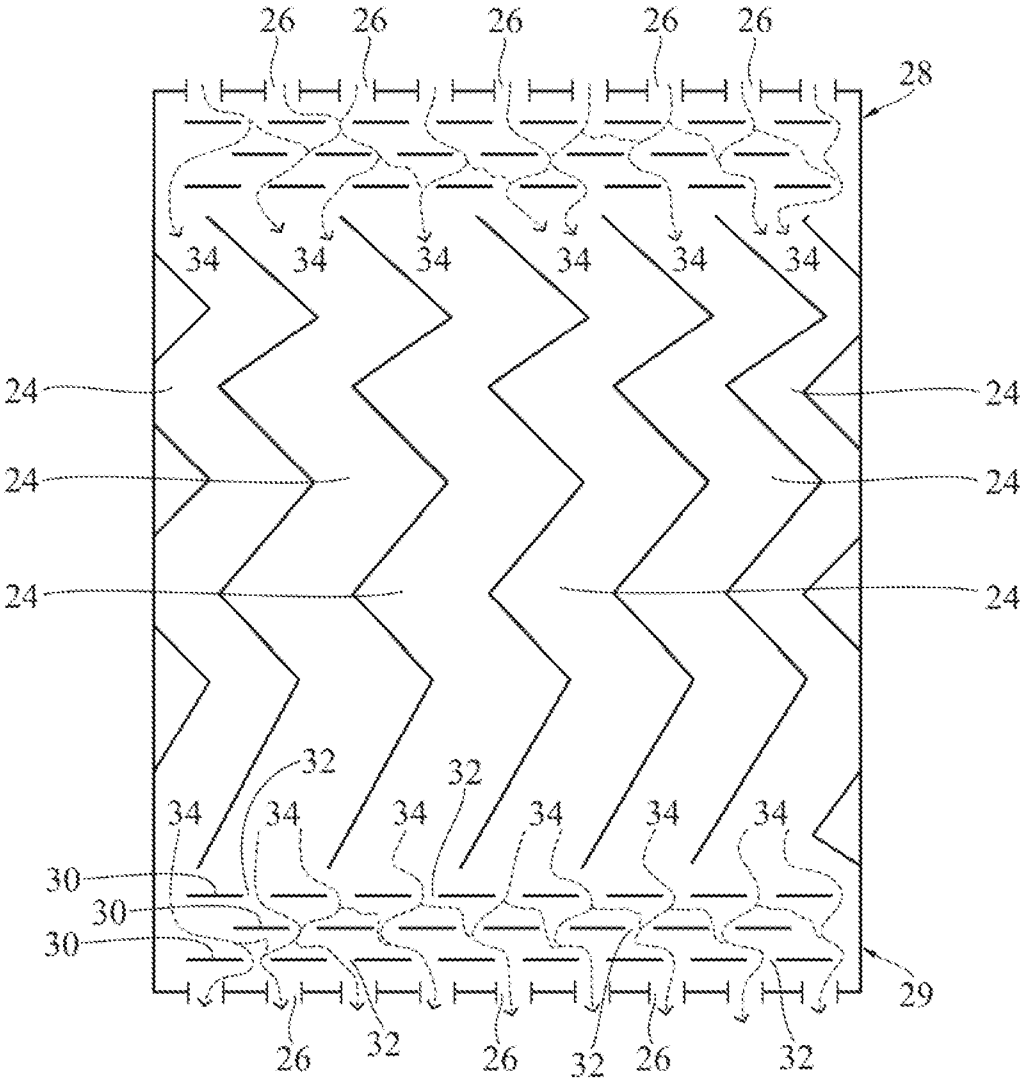
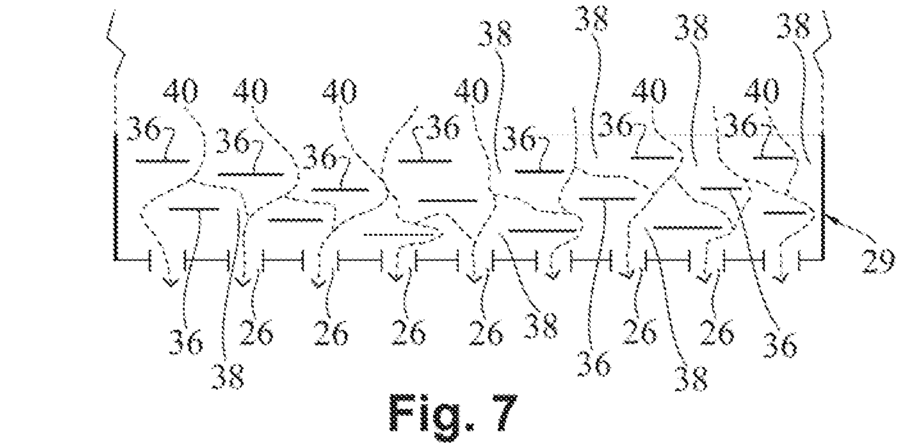
Fig. 7

DEAD AIR MASK FOR KILLING MICROORGANISMS IN AIR BREATHED BY A WEARER OF THE MASK

CROSS REFERENCE TO RELATED APPLICATIONS

This application is a domestic application that claims priority to, and the benefit of, International Patent Cooperation Treaty (PCT) Application No. PCT/US2021/023358, having the title of "Dead Air Mask For Killing Microorganisms In Air Breathed By A Wearer Of the Mask" filed on Mar. 19, 2021, which claims priority to U.S. Provisional Application No. 62/992,554, filed on Mar. 20, 2020, having the title of "Dead Air Mask For Killing Microorganisms In Air" and Provisional Application No. 63/155,608, filed on Mar. 2, 2021, having the title of "Dead Air Mask For Killing Microorganisms In Air Breathed By A Wearer Of the Mask". The disclosures of the prior applications are hereby incorporated by reference herein in their entireties.

TECHNICAL FIELD

The present disclosure relates to a mask that is wearable on the face of a person for killing microorganisms in the air that is breathed by the person through the mask. In particular, the disclosure relates to a mask that includes one or more ultraviolet (UV-C) light sources that emit anti-microbial light at a wavelength that kills microorganisms in the air breathed through the mask by the person wearing the mask.

BACKGROUND

Masks have been worn by people to protect themselves from breathing air containing harmful microorganisms. These microorganisms may include viruses, fungi, bacteria, and parasites. Many masks cover the mouth and nose of the wearer. Most accessible masks are made of cloth and include fabric having micro-filters. There is no evidence that such masks are effective at preventing all microorganisms from being breathed in by the wearer. Other masks have sought to employ ultraviolet (UV-C) light to kill the microorganisms. However, those masks are unable to assuredly prevent, in a simple and efficient manner, the ultraviolet (UV-C) light from harming the skin of the wearer. Moreover, existing ultraviolet (UV-C) light masks may not kill all of the microorganisms passing through the mask.

SUMMARY

The present disclosure discusses a microbe killing mask that is wearable on the face of a person. The mask may kill microorganisms in the air that is breathed by the person through the mask. The mask may have a light module including one or more airflow paths which extend between an inlet of the light module and an outlet thereof, and which receive the air breathed in and breathed out by the person. One or more ultraviolet (UV-C) light sources emit anti-microbial light into the airflow paths at a wavelength that kills microorganisms in the air passing along the airflow paths. Such a wavelength may be in the range of 200 nm to 300 nm. The airflow paths may have a zig-zag shape. This zig-zag shape increases the amount of time the air spends in the airflow paths, thus maximizing the exposure of the air passing in the airflow paths to the anti-microbial light before the air enters the mouth and/or nose of the person. This configuration greatly increases the likelihood that the irradiated air entering the mouth and/or nose of the person is completely free of harmful microorganisms. Further, the zig-zag shape of the airflow paths may disrupt laminar flow of the microorganisms, which could otherwise shield some microorganisms traveling in the center of the flow from the irradiated light. The present disclosure is thus an improvement over the known microbe killing masks.

The inlet and outlet ends of the light module may each include a light barrier comprising a staggered airflow path that allows irradiated air to pass through the light barrier, but blocks the anti-microbial light from passing through the light barrier and irradiating the face of the person. The light barrier may be formed of a plurality of walls having one or more slits through which the air passes. The slits of each wall are offset relative to the slits of an adjacent wall to form a staggered airflow path through the plurality of walls allowing air to pass through offset slits, but blocking the anti-microbial light from passing therethrough. Alternatively, the light barrier may be formed of rows of offset walls forming a staggered airflow path through the light barrier that allows the air to pass through, but blocks the anti-microbial light from passing through the light barrier. The light module thus protects the face of the person wearing the mask from the harmful anti-microbial light emitted from the ultraviolet (UV-C) light source. The present disclosure is thus an improvement over the known microbe killing masks in this regard as well.

The mask may be configured to have a relatively simple design in which the light module serves as the sole air inflow/outflow path into and out of the mask. That is, the one or more airflow paths receive both the air breathed in by the person wearing the mask and air breathed out by the person. As such, the air breathed in and breathed out by the person passes through the same airflow paths to be irradiated by the ultraviolet (UV-C) light source when entering and exiting the mask. Because of all of the air breathed in and out by the person wearing the mask passes through the same airflow paths and is irradiated by the ultraviolet (UV-C) light source, the mask eliminates the need for an air filter to catch microorganisms in the air passing into the mask.

Further, a side of the outlet of the light module may be exposed to the mouth and/or nose of the person wearing the mask and may include several openings or slits to provide for uninhibited airflow into and out of the outlet so that breathing by the person wearing the mask is not overly obstructed.

In one embodiment, a mask that is wearable on the face of a person comprises: a cover for covering at least one of the mouth and the nose of the person; a light module attached to the cover and comprising: an inlet for receiving air to be breathed in by the person, and an outlet that faces the person when the mask is on the face of the person; one or more airflow paths extending between the inlet and the outlet, the one or more airflow paths configured to receive at least the air to be breathed in by the person; an ultraviolet (UV-C) light source configured to emit anti-microbial light into the one or more airflow paths at a wavelength that kills microorganisms in the air in the one or more airflow paths; and a plurality of walls at each of the inlet and the outlet, wherein each of the plurality of walls comprises one or more slits through which the air passes, and the one or more slits of each wall are offset relative to the one or more slits of an adjacent wall to form staggered airflow paths through the plurality of walls that allow the air to pass through offset slits, but blocks the anti-microbial light from passing through the offset slits.

In an embodiment, each of the one or more airflow paths has a zig-zag shape.

In an embodiment, the mask further comprises a power source that supplies power to the ultraviolet (UV-C) light source.

In an embodiment, the ultraviolet (UV-C) light source comprises an LED.

In an embodiment, the ultraviolet (UV-C) light source emits the anti-microbial light at a wavelength in the range of 200 nm to 300 nm.

In an embodiment, the mask further comprises a fan proximate the inlet of the light module. In an embodiment, the fan includes: a sensor that detects an inhale and an exhale by the person when the mask is on the face of the person; and a motor that rotates the fan in a first rotation direction to help move the air toward the person with the inhale and in a second rotation direction to help move the air away from the person with the exhale.

In an embodiment, the ultraviolet (UV-C) light source comprises two ultraviolet (UV-C) light sources provided on opposing sides of the light module.

In an embodiment, the outlet is exposed to the face of the person when the mask is on the face of the person.

In an embodiment, the one or more airflow paths receive both the air to be breathed in by the person and air to be breathed out by the person.

In a further embodiment, a mask that is wearable on the face of a person comprises: a cover for covering at least one of the mouth and the nose of the person; a light module attached to the cover and comprising: an inlet for receiving air to be breathed in by the person, and an outlet that faces the person when the mask is on the face of the person; one or more airflow paths extending between the inlet and the outlet, the one or more airflow paths configured to receive at least the air to be breathed in by the person; an ultraviolet (UV-C) light source configured to emit anti-microbial light into the one or more airflow paths at a wavelength that kills microorganisms in the air in the one or more airflow paths; and a light barrier located on each end of the one or more airflow paths and into which the one or more airflow paths open, wherein the light barrier comprises rows of offset walls forming a plurality of staggered airflow paths through the light barrier that allow the air to pass therethrough, but blocks the anti-microbial light from passing through the light barrier.

In an embodiment, each of the one or more airflow paths has a zig-zag shape.

In an embodiment, one of the light barriers is exposed to the face of the person when the mask is on the face of the person, and includes multiple openings through which the plurality of staggered airflow paths pass to and from the face of the person.

In an embodiment, the mask further comprises a power source that supplies power to the ultraviolet (UV-C) light source.

In an embodiment, the ultraviolet (UV-C) light source comprises an LED.

In an embodiment, the ultraviolet (UV-C) light source emits the anti-microbial light at a wavelength in the range of 200 nm to 300 nm.

In an embodiment, the mask further comprises a fan proximate the inlet of the light module. In an embodiment, the fan includes: a sensor that detects an inhale and an exhale by the person when the mask is on the face of the person; and a motor that rotates the fan in a first rotation direction to help move the air toward the person with the inhale and in a second rotation direction to help move the air away from the person with the exhale.

In an embodiment, the ultraviolet (UV-C) light source comprises two ultraviolet (UV-C) light sources provided on opposing sides of the light module.

In an embodiment, the one or more airflow paths receive both the air to be breathed in by the person and air to be breathed out by the person.

BRIEF DESCRIPTION OF THE FIGURES

Various embodiments are hereafter described in detail and with reference to the drawings wherein like reference characters designate like or similar elements throughout the several figures and views that collectively comprise the drawings.

FIG. 6 is a view showing the configuration of a portion of the light module, according to one embodiment.

FIG. 7 is a view showing the configuration of a portion of the light module, according to another embodiment.

DETAILED DESCRIPTION

Before describing selected embodiments of the present disclosure in detail, it is to be understood that the present invention is not limited to the particular embodiments described herein. The disclosure and description herein is illustrative and explanatory of one or more presently preferred embodiments and variations thereof, and it will be appreciated by those skilled in the art that various changes in the design, organization, means of operation, structures and location, methodology, and use of mechanical equivalents may be made without departing from the spirit of the invention.

It should also be understood that the drawings are intended to illustrate and plainly disclose presently preferred embodiments to one of skill in the art, but are not intended to be manufacturing level drawings or renditions of final products and may include simplified conceptual views to facilitate understanding or explanation. As well, the relative size and arrangement of the components may differ from that shown and still operate within the spirit of the invention.

Moreover, it will be understood that various directions such as “upper”, “lower”, “bottom”, “top”, “left”, “right”, and so forth are made only with respect to explanation in conjunction with the drawings, and that components may be oriented differently, for instance, during transportation and manufacturing as well as operation. Because many varying and different embodiments may be made within the scope of the concept(s) herein taught, and because many modifications may be made in the embodiments described herein, it is to be understood that the details herein are to be interpreted as illustrative and non-limiting.

Figure 1:
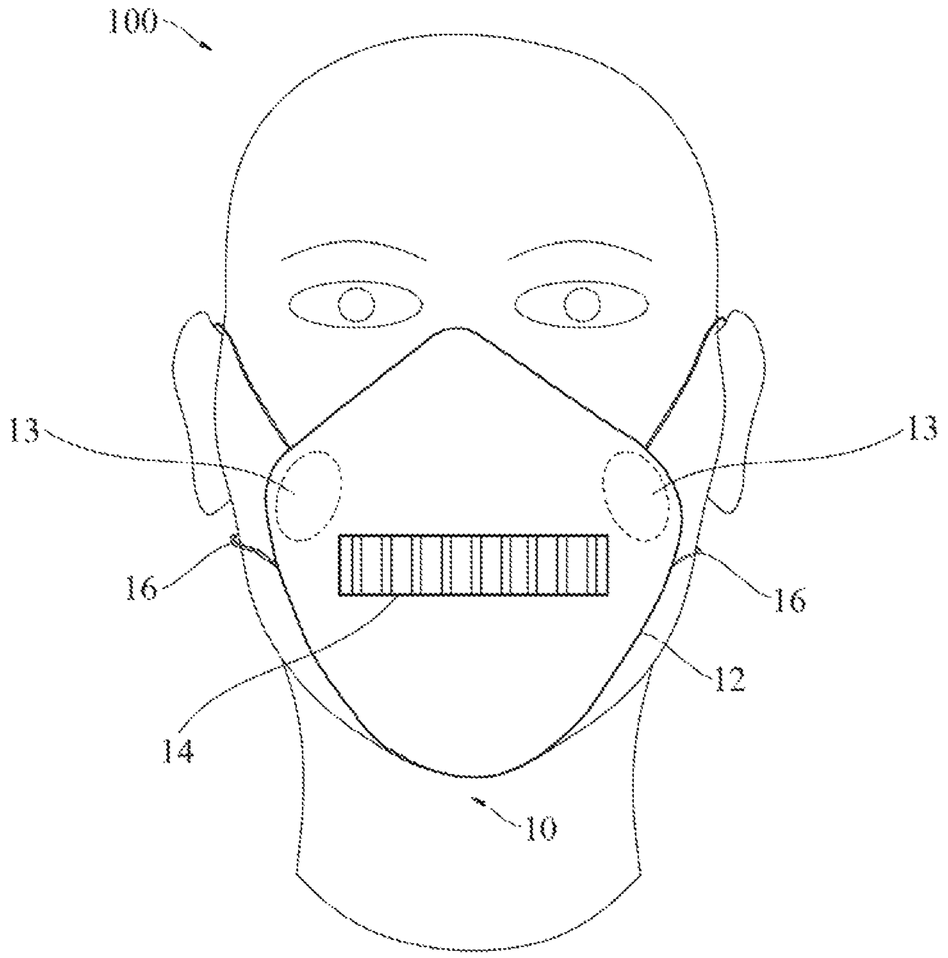
FIG. 1 is a frontal view of a person wearing a mask that kills microorganisms, according to one embodiment.

FIG. 1 illustrates one embodiment of a dead air mask 10 for killing microorganisms in the air breathed through the mask 10 by the person 100 wearing the mask 10. The dead air mask 10 is shown being worn on the face of a person 100 in a frontal view perspective. The mask 10 may be attached to the person with one or more straps 16 for fitting around the ears of the person 100 as shown in FIG. 1, or alternatively the straps 16 may be configured to wrap around the head of the person 100. In either case, the cover 12 of the mask 10 is adapted to cover at least the mouth of the person 100, and preferable both the mouth and nose of the person 100 as shown in FIG. 1. The cover 12 may be form fitting to the face of the person 100 so that no air is able to escape from between the cover 12 and the face of the person 100. That is, the cover 12 may form an air-tight seal with the face of the person 100 when the mask 10 is worn by the person 100. The cover 12 may be made of silicon, rubber, plastic and/or other material, and may be heated, e.g., in hot water, to be form fitted to the face of the person 100 in order to provide the air-tight seal when the mask 10 is worn by the person 100.

In one embodiment, the cover 12 may include an expandable pocket 13 on each side of the cover 12, so that each expandable pocket 13 is on one side of the mouth of the person 100 when the mask 10 is on the face of the person 100. Each expandable pocket 13 is configured to expand in response to a sneeze or cough of the person 100, and then to slowly contract back to its original shape while slowly pushing the exhaled air out of the front of the mask 10 through a light module 14 (discussed below). In other words, the expandable pockets 13 absorb the extreme pressure from the sneeze or cough and channel that pressure (along with the air) slowly out through the front of the mask 10.

Figure 2:
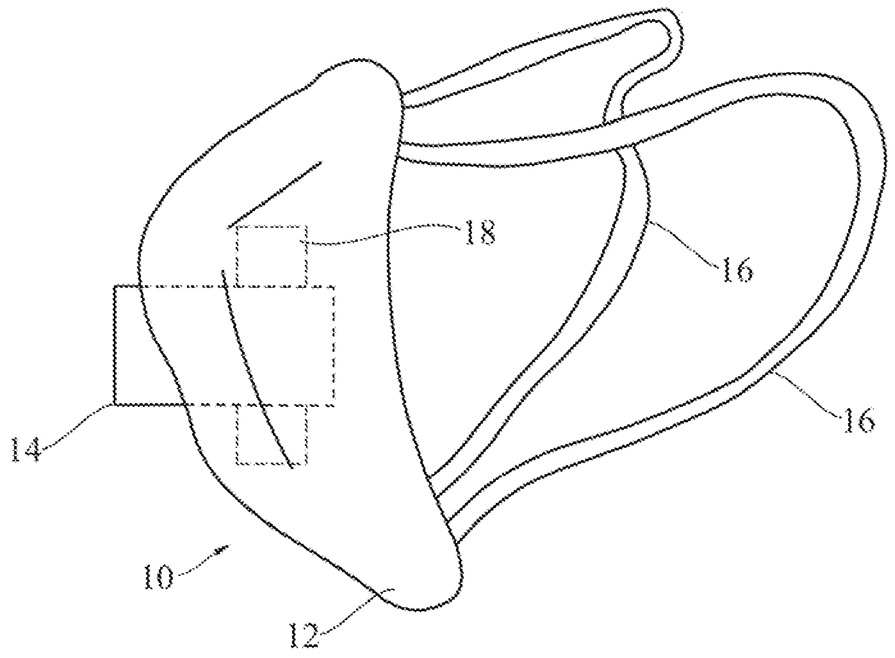
FIG. 2 is a side view of the mask, according to one embodiment.
Figure 3:
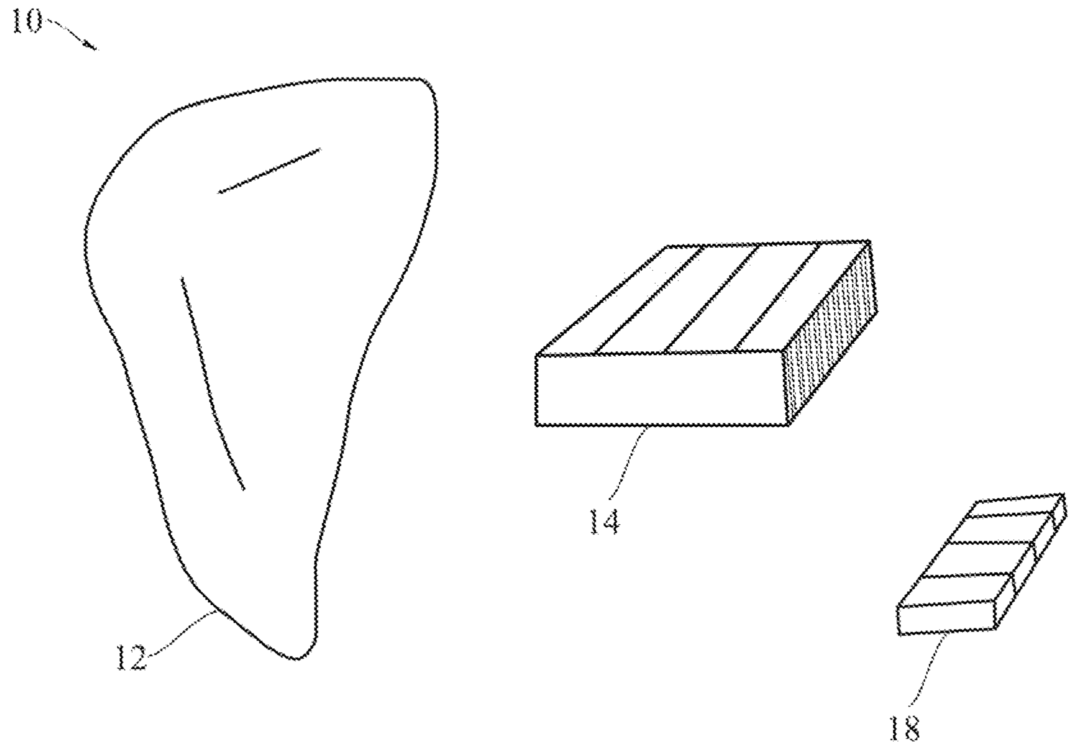
FIG. 3 is an exploded view of the mask, according to one embodiment.

In order to kill microorganisms in the air that is breathed by the person 100 through the mask 10, the mask 10 includes a light module 14 attached to the cover 12. As shown in FIG. 2, the light module 14 may protrude from the front of the cover 12. Alternatively, the inlet end of the light module 14 may be flush with the cover 12. In either case, the inlet end of the light module 14 may be exposed on the front of the cover 12 in order to receive air to be breathed in by the person 100, as discussed in detail below. FIG. 3 shows some of the component parts of the mask 10 in an exploded view, namely, the cover 12, the light module 14, and a power source 18 that provides power to the light module 14. In one embodiment, the power source 18 may be battery or battery pack, such as a lithium ion battery pack. The battery or battery pack may be rechargeable or replaceable. An outlet end of the light module 14, which is opposite to the inlet end, faces the mouth of the person 100 when the mask 10 is on the face of the person 100. In an embodiment, the outlet end may be exposed to the face of the person 100, as discussed below.

Figure 4:
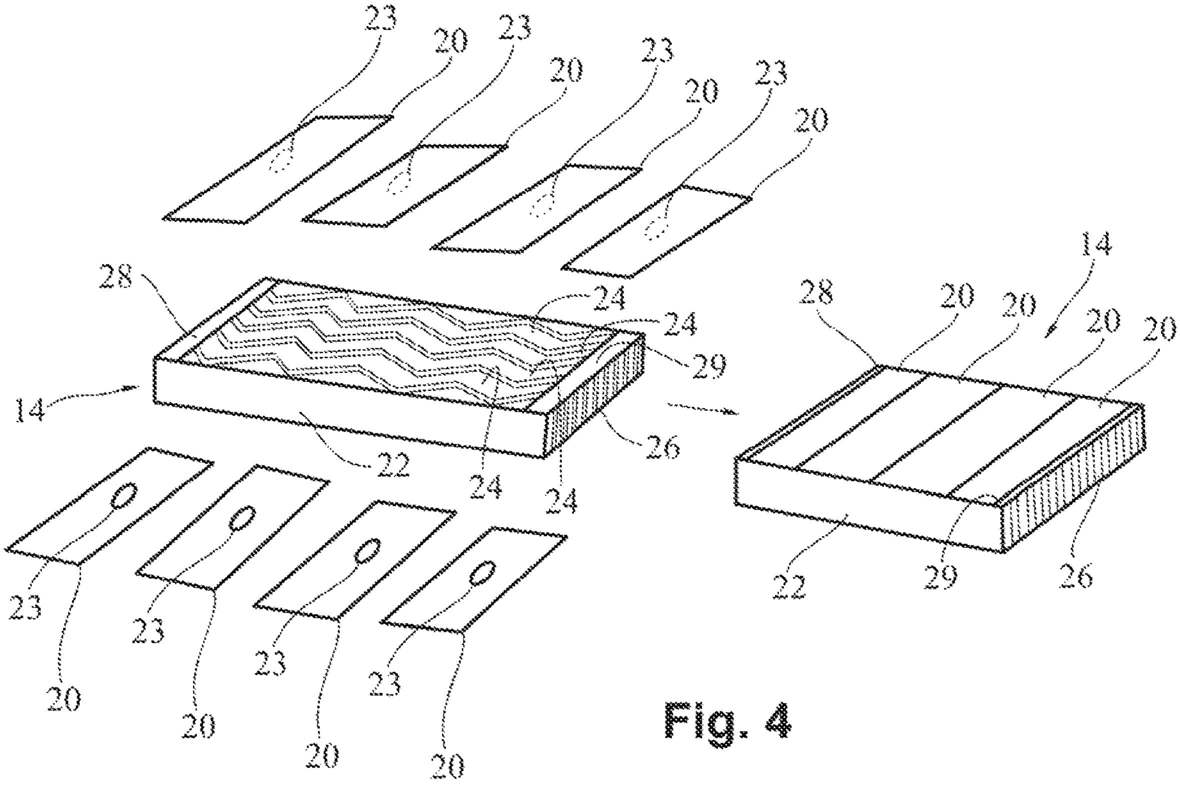
FIG. 4 is an exploded view of light module of the mask, according to one embodiment.

FIG. 4 shows an embodiment of the light module 14 of the mask 10. The light module 14 is shown having a substantially rectangular shape in this illustrated embodiment, but the overall shape is not limited to a rectangle or square. In some embodiments, the light module 14 may have a circular, elliptical, or other polygonal shape that may contour to the cover 12 of the mask 10. The light module 14 may be composed of a housing 22 that includes airflow paths 24 defined by walls having a zig-zag orientation so that the airflow paths 24 have a zig-zag shape. The number of airflow paths 24 is not particularly limiting, and may range from one to ten zig-zagged airflow paths 24. The airflow paths 24 extend from an inlet 28 on one end of the housing 22 to an outlet 29 on the opposite end of the housing 22. The inlet 28 includes a plurality of openings 26 and is configured to receive air to be breathed in by the person 100 wearing the mask 10. The outlet 29 faces the person 100 when the mask 10 is on the face of the person 100, and also includes a plurality of openings 26. In this configuration, the airflow paths 24 are configured to receive the air to be breathed in by the person 100 through the openings 26 in the inlet 28 and guide the breathed-in air through the openings 26 in the outlet 29 to the mouth and/or nose of the person 100 wearing the mask 10. Similarly, the airflow paths 24 are configured to receive the air to be breathed out by the person 100 through the openings 26 in the outlet 28 and guide the breathed-out air through the openings 26 in the inlet 28 and out of the light module 14/mask 10. The airflow paths 24 thus receive both the air to be breathed in by the person 100 and air to be breathed out by the person 100.

Each of the top and bottom of the light module 14 may be formed of one or more panels 20 that enclose the airflow paths 24 within the light module 14. The light module 14 is thus sealed except for the openings 26 in the inlet 28 and the outlet 29. One or more of the panels 20 may include an ultraviolet (UV-C) light source 23 configured to emit anti-microbial light into the airflow paths 24 at a wavelength that kills microorganisms in the air irradiated in the airflow paths 24 by the anti-microbial light. The ultraviolet (UV-C) light source 23 may be one or more LEDs. In another embodiment, the ultraviolet (UV-C) light source 23 may be a light bulb. The ultraviolet (UV-C) light source 23 may emit blue light. In one embodiment, the ultraviolet (UV-C) light source 23 emits the anti-microbial light at a wavelength in the range of 200 nm to 300 nm. For instance, the ultraviolet (UV-C) light source 23 may emit anti-microbial light at a wavelength of 262 nm. Both of the top panels 20 and the bottom panels 20 of the light module 14 may include the ultraviolet (UV-C) light source 23, so that the ultraviolet (UV-C) light source 23 is provided on opposing sides of the light module 14. Alternatively, only the top panels 20 may include the ultraviolet (UV-C) light source 23 while the bottom panels 20 do not, and vice versa. Further, where multiple panels 20 are used, one or more of the panels 20 may include the ultraviolet (UV-C) light source 23, and some may not include the ultraviolet (UV-C) light source 23. The shape and size of the ultraviolet (UV-C) light source 23 are not particularly limited, and are simply required to emit an appropriate amount of anti-microbial light into the airflow paths 24 to kill microorganisms in the air irradiated in the airflow paths 24. The housing 22 protects the ultraviolet (UV-C) light source 23 from physical damage. With this orientation, the photons emitted from the ultraviolet (UV-C) light source 23 are directed toward the airflow paths 24 such that air passing through the light module 14 is irradiated by the anti-microbial light. In one embodiment, the light module may be 3 cm to 10 cm or more in length, and may have a width of the same dimensions. In an embodiment, the ultraviolet (UV-C) light source 23 may be glued to the panel 20 with a heat-resistant glue. In other embodiments, the ultraviolet (UV-C) light source 23 may be attached to the panel 20 with tape, or mechanically. The power source 18 may supply power to the ultraviolet (UV-C) light source 23.

Figure 5:
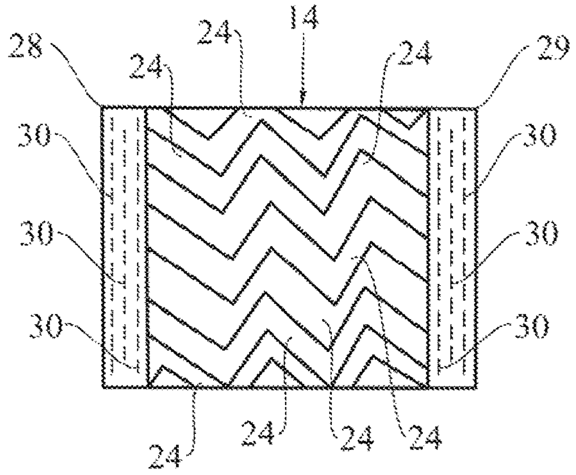
FIG. 5 is a cross-sectional plan view of light module of the mask, according to one embodiment.

FIG. 5 is a cross-sectional plan view of the light module 14, and shows the zig-zag airflow paths 24 extending between the inlet 28 of the light module 14 and the outlet 29. The zig-zag shape of the airflow paths 24 may disrupt laminar flow of the microorganisms in the air moving in the airflow paths 24. The laminar flow could otherwise shield some microorganisms traveling in the center of the airflow from being irradiated by the anti-microbial light from the ultraviolet (UV-C) light source 23. The zig-zag shape of the airflow paths 24 also increases the amount of time the air spends in the airflow paths 24, thus maximizing the exposure of the air passing in the airflow paths 24 to the anti-microbial light before the air enters the mouth and/or nose of the person 100. Accordingly, the probability that some of the harmful microorganisms in the air will reach the person's mouth or nose without being irradiated (i.e., killed) by the anti-microbial light is greatly diminished, if not completely eliminated. This configuration greatly increases the likelihood that the irradiated air entering the mouth and/or nose of the person 100 is completely free of harmful microorganisms. That is, the zig-zag shape of the airflow paths 24 significantly increases the probability that all microorganisms in the air breathed in by the person 100 through the mask will be killed before being inhaled through the mask by the person 100. In some embodiments, the interior surfaces of the housing 22 and/or the walls of the airflow paths 24 may have, or be formed of, mirrors. The mirrors may better reflect and/or ricochet rays of the ultraviolet (UV-C) light and thus increase exposure of pathogens in the air irradiated in the airflow paths 24 to the ultraviolet (UV-C) light. As an alternative to mirrors, the interior surfaces of the housing 22 and/or the walls of the airflow paths 24 may include a reflective coating, or may be formed of a chrome material. Similarly, the interior surfaces of the top and bottom panels 20 of the light module 14 may have, or be formed of, mirrors; may include a reflective coating; or may have, or be formed of, a chrome material.

FIG. 6 shows a close-up view of the outlet 29 of the light module 14, according to one embodiment. It is noted, however, that the inlet 28 of the light module 14 may the same configuration as the outlet 29. The outlet 29 may include a plurality of walls 30 that each have one or more slits 32 through which the air breathed in and the air breathed out passes. The slits 32 of each wall 30 are offset relative to the slits 32 of an adjacent wall 30 to form staggered airflow paths 34 through the plurality of walls 30. The staggered airflow paths 34 allow the air to pass through offset slits 32, but blocks the anti-microbial light emitted by the ultraviolet (UV-C) light source 23 from passing through the offset slits 32 and irradiating the face of the person 100 wearing the mask 10. The staggered airflow paths 34 thus allow the air to pass to and from the person through the offset slits 32 while protecting the person 100 from the harmful anti-microbial light. In like manner, the inlet 28 having this same configuration prevents harmful ultraviolet (UV-C) light from exiting the inlet 28 of the light module 14 and impacting other people. In one embodiment, the light module 14 may be comprised of four walls 30 as shown in FIG. 6. However, the number of walls 30 is not particularly limiting, and the number of walls 30 may be less than or greater than four. Nor is the number of slits 32 limiting to this disclosure. What is important is that the number of walls 30 and slits 32 be sufficient to allow air to pass through the outlet 29 while blocking harmful anti-microbial light from passing therethrough. Further, the distance between the walls 30 is not particularly limited in this disclosure, only that the distance allows air to freely pass through the slits 32 to the openings 26. In an embodiment, the walls 30 may be spaced 0.1 mm to 5 mm from each other. The outlet 29 may be exposed to the face of the person 100 when the mask 10 is on the face of the person 100. Thus, the openings 26 at the outlet 29 also are exposed to the face of the person 100 when the mask 10 is on the face of the person 100. The mask 10 is thus configured so that all of the air breathed in by the person wearing the mask 10 enters only into the inlet 28 of the light module 14, passes through the airflow paths 24 while being irradiated by the anti-microbial light from the ultraviolet (UV-C) light source 23, and exits through the outlet 29. Similarly, all of the air breathed out by the person wearing the mask 10 enters only into the outlet 29, passes through the airflow paths 24 while being irradiated by the anti-microbial light from the ultraviolet (UV-C) light source 23, and exits through the inlet 28 and out of the mask 10. In some embodiments, the surface of the walls 30 that faces the airflow paths 24 may have, or be formed of, mirrors; may include a reflective coating; or may have, or be formed of, a chrome material. On the other hand, the (opposite) surface of the walls 30 that faces the openings 26 of the outlet 29 may have a black or dark color, and/or may include anti-reflective material. This configuration may help reflect and/or ricochet rays of the ultraviolet (UV-C) light in the outlet 29 on the side of the walls 30 that faces the airflow paths 24, while not promoting such action on the side of the walls 30 that face the wearer 100 of the mask 10.

FIG. 7 shows a close-up view of the outlet 29 of the light module 14, according to another embodiment. The inlet 28 of the light module 14 may the same configuration as the outlet 29 of this embodiment, or may have the configuration shown in FIG. 6, and vice versa. In this embodiment, the outlet 29 forms a light barrier into which the airflow paths 24 open. The light barrier (outlet 29) comprises rows of offset walls 36 forming a plurality of staggered airflow paths 40 through gaps 38 between the offset walls 36. The gaps 38 allow passage of the air breathed in and out by the person, but block the anti-microbial light emitted by the ultraviolet (UV-C) light source 23 from passing through the staggered airflow paths 40 and irradiating the face of the person 100 wearing the mask 10. The staggered airflow paths 40 thus allow the air to pass to and from the person through the gaps 38 while protecting the person 100 from the harmful anti-microbial light. In one embodiment, the light barrier may be comprised of three rows of offset walls 36 as shown in FIG. 7. However, the number of rows of offset walls 36 is not particularly limiting, and the number of walls may be less than or greater than three. Nor are the number walls 36 and corresponding gaps 38 between the walls 36 limiting to this disclosure. What is important is that the number of walls 36 and corresponding gaps 38 be sufficient to allow air to pass through the outlet 29 while blocking harmful anti-microbial light from passing therethrough. Further, the plurality of walls 36 may not be located in uniform rows, and may be arranged somewhat randomly throughout the light barrier (outlet 29). The distance between the walls 36 is not particularly limited in this disclosure, only that the distance allows air to freely pass through the gaps 38 to the openings 26. In an embodiment, the walls 36 may be spaced 0.1 mm to 5 mm from each other. As in the FIG. 6 embodiment, the outlet 29 may be exposed to the face of the person 100 when the mask 10 is on the face of the person 100. Thus, the openings 26 at the outlet 29 also are exposed to the face of the person 100 when the mask 10 is on the face of the person 100. The mask 10 is thus configured so that all of the air breathed in by the person wearing the mask 10 enters only into the inlet 28 of the light module 14, passes through the airflow paths 24 while being irradiated by the anti-microbial light from the ultraviolet (UV-C) light source 23, and exits through the outlet 29. Similarly, all of the air breathed out by the person wearing the mask 10 enters only into the outlet 29, passes through the airflow paths 24 while being irradiated by the anti-microbial light from the ultraviolet (UV-C) light source 23, and exits through the inlet 28 and out of the mask 10. In some embodiments, the surface of the walls 30 that faces the airflow paths 24 may have, or be formed of, mirrors; may include a reflective coating; or may have, or be formed of, a chrome material. On the other hand, the (opposite) surface of the walls 36 that faces the openings 26 of the outlet 29 may have a black or dark color, and/or may include anti-reflective material. This configuration may help reflect and/or ricochet rays of the ultraviolet (UV-C) light in the outlet 29 on the side of the walls 36 that faces the airflow paths 24, while not promoting such action on the side of the walls 36 that face the wearer 100 of the mask 10.

Figure 8:
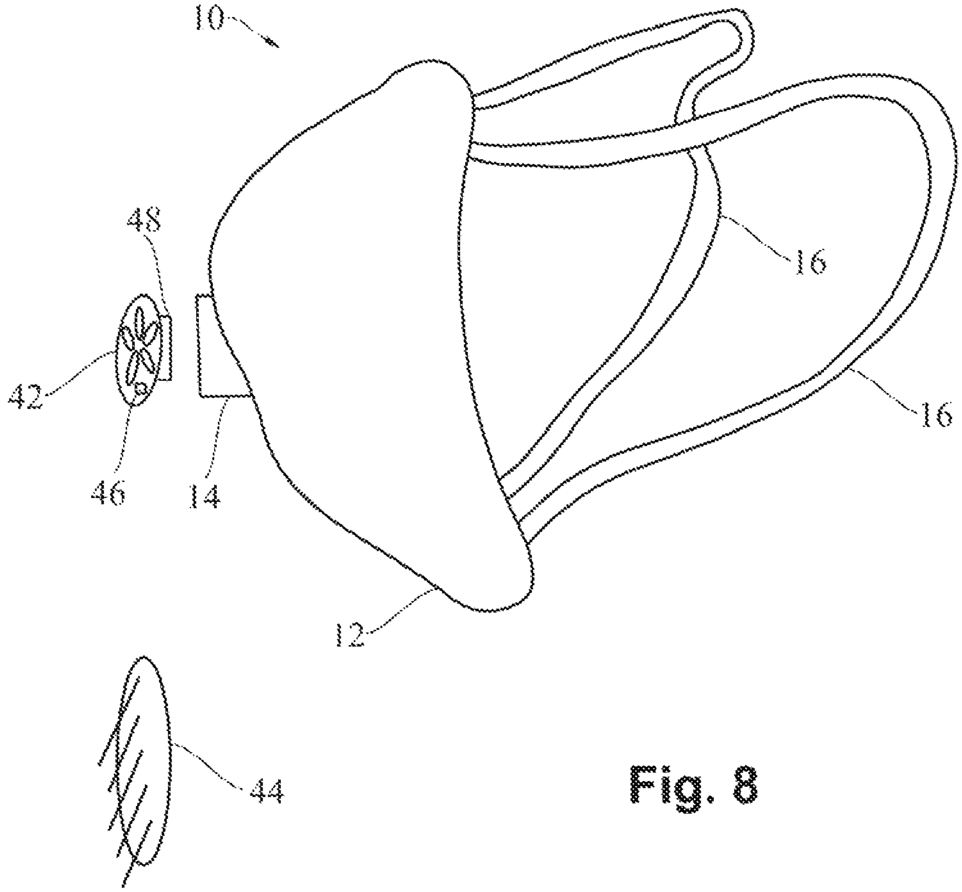
FIG. 8 is a side view of the mask showing additional components, according to an embodiment.

FIG. 8 shows that the mask 10 may have additional components. In particular, the mask 10 may include a fan 42. The fan 42 may be configured to rotate in response to an inhale or an exhale of the person 100 when the mask 10 is on the face of the person 100. The fan 42 thus assists the breathing of the person 100. In an embodiment, the fan 42 may be attachable to the inlet 28 of the light module 14 as shown in FIG. 8. Attentively, the fan 42 may be attachable to the outlet 29 of the light module 14. The fan 42 may include a sensor 46 that detects an inhale and an exhale by the person 100 when the mask 10 is on the face of the person 100. A motor 48 of the fan 42 may rotate the fan 42 in a first rotation direction to help move the air toward the person 100 with the inhale, and in a second rotation direction to help move the air away from the person 100 with the exhale. Further, the fan 42 may be part of an assembly that includes a visual indicator (not shown) that indicates when the person 100 wearing the mask 10 is inhaling or exhaling. For instance, the visual indicator may be a light that turns green when an inhale is detected by the sensor 46 and the motor 48 rotates the fan 42 in one direction, and turns red when an exhale is detected by the sensor 46 and the motor 48 rotates the fan 42 in an opposite direction.

In addition, the mask 10 may include a detachable vent cover 44 that is attachable to the inlet 28 of the light module 14. The detachable vent cover 44 may include movable louvers that open and close. The louvers may be sprung at a 45 degrees angle downward, as shown in FIG. 8, to prevent rain from entering the light module 14. The louvers may be opened and closed manually. In an embodiment, the detachable vent cover 44 may include a smart chip or sensor that can detect the pressure of a sneeze or a cough of the person 100 wearing the mask 10, and control the louvers to close when the sneeze or a cough occurs, or when a deep inhale before a sneeze occurs, thus forcing the exhaled air of the sneeze or a cough into the expandable pockets 13. Alternatively, the louvers may be manually closed by the person when the sneeze or a cough occurs.

It is to be noted that each component of the mask 10 may be modular, so that the light module 14, the power source 18, the fan 42, and the detachable vent cover 44 may be detachable from the mask 10. This allows the component modular parts to be detached from the mask for repair or replacement. In addition, the mask 10 may accommodate more than one light module 14. For instance, multiple light modules 14 may be stackable (not shown) within the mask 10. In such a case, an additional power source 18 (more several power sources 18) may be provided to help supply power to the multiple light modules 14. The multiple light modules 14 and power sources 18 may be sized to fit within the mask 10.

Although several preferred embodiments have been illustrated in the accompanying drawings and describe in the foregoing specification, it will be understood by those of skill in the art that additional embodiments, modifications and alterations may be constructed from the principles disclosed herein.

What is claimed is:

1. A mask that is wearable on the face of a person, the mask comprising:
- a cover for covering at least one of the a mouth and the a nose of the person;
- a light module attached to the cover and comprising:
  - an inlet for receiving air to be breathed in by the person, and an outlet that faces the person when the mask is on the face of the person;
  - one or more airflow paths extending between the inlet and the outlet, the one or more airflow paths configured to receive at least the air to be breathed in by the person;
  - an ultraviolet (UV-C) light source configured to emit anti-microbial light into the one or more airflow paths at a wavelength that kills microorganisms in the air in the one or more airflow paths; and
  - a plurality of walls at each of the inlet and the outlet, wherein each of the plurality of walls comprises one or more slits through which the air passes such that the one or more slits are located at opposite ends of the one or more airflow paths, and the one or more slits of each wall are offset relative to the one or more slits of an adjacent wall to form staggered airflow paths through the plurality of walls that allow the air to pass through offset slits, but blocks the anti-microbial light from passing through the offset slits.

2. The mask according to claim 1, wherein each of the one or more airflow paths has a zig-zag shape.

3. The mask according to claim 1, further comprising a power source that supplies power to the ultraviolet (UV-C) light source.

4. The mask according to claim 1, wherein the ultraviolet (UV-C) light source comprises an LED.

5. The mask according to claim 1, wherein the ultraviolet (UV-C) light source emits the anti-microbial light at a wavelength in the range of 200 nm to 300 nm.

6. The mask according to claim 1, further comprising a fan proximate the inlet of the light module.

7. The mask according to claim 6, wherein the fan includes:
- a sensor that detects an inhale and an exhale by the person when the mask is on the face of the person; and
- a motor that rotates the fan in a first rotation direction to help move the air toward the person with the inhale and in a second rotation direction to help move the air away from the person with the exhale.

8. The mask according to claim 1, wherein the ultraviolet (UV-C) light source comprises two ultraviolet (UV-C) light sources provided on opposing sides of the light module.

9. The mask according to claim 1, wherein the outlet is exposed to the face of the person when the mask is on the face of the person.

10. The mask according to claim 1, wherein the one or more airflow paths receive both the air to be breathed in by the person and air to be breathed out by the person.

11. A mask that is wearable on the face of a person, the mask comprising:
- a cover for covering at least one of the a mouth and the a nose of the person;
- a light module attached to the cover and comprising:
  - an inlet for receiving air to be breathed in by the person, and an outlet that faces the person when the mask is on the face of the person;

one or more airflow paths extending between the inlet and the outlet, the one or more airflow paths configured to receive at least the air to be breathed in by the person;

an ultraviolet (UV-C) light source configured to emit anti-microbial light into the one or more airflow paths at a wavelength that kills microorganisms in the air in the one or more airflow paths; and a light barrier located on each end of the one or more airflow paths and into which the one or more airflow paths open, wherein the light barrier on each end of the one or more airflow paths comprises rows of offset walls forming a plurality of staggered airflow paths through the light barrier that allow the air to pass therethrough, but blocks the anti-microbial light from passing through the light barrier.

12. The mask according to claim 11, wherein each of the one or more airflow paths has a zig-zag shape.

13. The mask according to claim 11, wherein one of the light barriers is exposed to the face of the person when the mask is on the face of the person, and includes multiple openings through which the plurality of staggered airflow paths pass to and from the face of the person.

14. The mask according to claim 11, further comprising a power source that supplies power to the ultraviolet (UV-C) light source.

15. The mask according to claim 11, wherein the ultraviolet (UV-C) light source comprises an LED.

16. The mask according to claim 11, wherein the ultraviolet (UV-C) light source emits the anti-microbial light at a wavelength in the range of 200 nm to 300 nm.

17. The mask according to claim 11, further comprising a fan proximate the inlet of the light module.

18. The mask according to claim 17, wherein the fan includes:

a sensor that detects an inhale and an exhale by the person when the mask is on the face of the person; and a motor that rotates the fan in a first rotation direction to help move the air toward the person with the inhale and in a second rotation direction to help move the air aw away from the person with the exhale.

19. The mask according to claim 11, wherein the ultraviolet (UV-C) light source comprises two ultraviolet (UV-C) light sources provided on opposing sides of the light module.

20. The mask according to claim 11, wherein the one or more airflow paths receive both the air to be breathed in by the person and air to be breathed out by the person.

* * * * *